(12) United States Patent
Seip et al.

(10) Patent No.: US 10,300,308 B2
(45) Date of Patent: May 28, 2019

(54) SYSTEM, APPARATUS AND METHOD FOR HIGH-INTENSITY FOCUSED ULTRASOUND (HIFU) AND/OR ULTRASOUND DELIVERY WHILE PROTECTING CRITICAL STRUCTURES

(71) Applicant: SonaCare Medical, LLC, Charlotte, NC (US)

(72) Inventors: Ralf Seip, Indianapolis, IN (US); Narendra Sanghvi, Indianapolis, IN (US); Roy Carlson, New Palestine, IN (US); Rodrigo Chaluisan, Charlotte, NC (US); Adam Morris, Charlotte, NC (US); Mark Carol, Cornelius, NC (US)

(73) Assignee: Sonacare Medical, LLC, Charlotte, NC (US)

( * ) Notice: Subject to any disclaimer, the term of this patent is extended or adjusted under 35 U.S.C. 154(b) by 0 days.

(21) Appl. No.: 15/709,917

(22) Filed: Sep. 20, 2017

(65) Prior Publication Data
US 2018/0085606 A1    Mar. 29, 2018

Related U.S. Application Data

(60) Provisional application No. 62/398,752, filed on Sep. 23, 2016.

(51) Int. Cl.
*A61N 7/02* (2006.01)
*B06B 1/02* (2006.01)
*A61N 7/00* (2006.01)

(52) U.S. Cl.
CPC .............. *A61N 7/02* (2013.01); *B06B 1/0207* (2013.01); *A61N 2007/0034* (2013.01);
(Continued)

(58) Field of Classification Search
CPC .............. A61N 7/02; A61N 2007/0095; A61N 2007/0091; A61N 2007/0034; B06B 1/0207; B06B 2201/76
(Continued)

(56) References Cited

U.S. PATENT DOCUMENTS 6,685,640 B1    2/2004  Fry et al.
7,559,905 B2    7/2009  Kagosaki et al.
(Continued)

FOREIGN PATENT DOCUMENTS

CA    2699408 A1    9/2008
CA    2706563 A1    6/2009
(Continued)

OTHER PUBLICATIONS

Zderic et al., Prevention of post-focal thermal damage by formation of bubbles at the focus during high intensity focused ultrasound therapy, Med. Phys. 35 (10), Oct. 2008.
(Continued)

*Primary Examiner* — Sanjay Cattungal
(74) *Attorney, Agent, or Firm* — Mark T. Vogelbacker; Eckert Seamans Cherin & Mellott, LLC

(57) ABSTRACT

A method for delivering ultrasound can include positioning at least a focal zone of a transducer of an ultrasound probe proximate to targeted tissue of a patient. The method can include supplying power to the transducer to deliver ultrasound energy from the transducer to a first portion of the targeted tissue for a predetermined amount of time to create a first focal lesion in the targeted tissue. The method can include at least temporarily ceasing power to the transducer so as to at least temporarily cease delivery of ultrasound energy from the transducer to the targeted tissue. The method can include supplying power to the transducer to deliver ultrasound energy from the transducer to the targeted
(Continued)

tissue at least substantially continuously and along a predefined treatment path.

20 Claims, 10 Drawing Sheets

(52) U.S. Cl.
CPC ............. *A61N 2007/0091* (2013.01); *A61N 2007/0095* (2013.01); *B06B 2201/76* (2013.01)

(58) Field of Classification Search
USPC .................................................. 600/437–469
See application file for complete search history.

(56) References Cited

U.S. PATENT DOCUMENTS

| | | | |
|---|---|---|---|
| 7,615,015 B2 | 11/2009 | Coleman | |
| 7,662,114 B2 | 2/2010 | Seip et al. | |
| 8,038,631 B1 | 10/2011 | Sanghvi et al. | |
| 8,088,067 B2* | 1/2012 | Vortman | A61N 7/02 |
| | | | 382/128 |
| 8,162,858 B2 | 4/2012 | Manna | |
| 8,235,902 B2 | 8/2012 | Chen et al. | |
| 8,622,937 B2* | 1/2014 | Weng | A61B 8/12 |
| | | | 600/439 |
| 9,095,695 B2* | 8/2015 | Fedewa | A61N 7/02 |
| 9,283,035 B2 | 3/2016 | Lanphere et al. | |
| 9,409,041 B2 | 8/2016 | Fedewa et al. | |
| 9,457,202 B2 | 10/2016 | Sanghvi et al. | |
| 2005/0228283 A1* | 10/2005 | Gifford | A61B 8/12 |
| | | | 600/459 |
| 2005/0240127 A1* | 10/2005 | Seip | A61N 7/02 |
| | | | 601/2 |
| 2008/0015435 A1 | 1/2008 | Cribbs et al. | |
| 2010/0217162 A1 | 8/2010 | Hissong et al. | |
| 2010/0241005 A1 | 9/2010 | Darlington et al. | |
| 2011/0066085 A1 | 3/2011 | Weng et al. | |
| 2011/0125143 A1 | 5/2011 | Gross et al. | |
| 2013/0018285 A1* | 1/2013 | Park | A61N 7/02 |
| | | | 601/2 |
| 2013/0023862 A1* | 1/2013 | Marrouche | A61N 7/02 |
| | | | 606/3 |
| 2013/0096552 A1 | 4/2013 | Brace et al. | |
| 2014/0058293 A1 | 2/2014 | Hynynen et al. | |
| 2014/0081301 A1 | 3/2014 | Tran et al. | |
| 2014/0200489 A1* | 7/2014 | Behar | A61N 7/02 |
| | | | 601/3 |
| 2014/0236050 A1* | 8/2014 | Lee | A61N 7/02 |
| | | | 601/3 |
| 2014/0243677 A1 | 8/2014 | Johnson et al. | |
| 2014/0277035 A1 | 9/2014 | Strait et al. | |
| 2014/0330124 A1* | 11/2014 | Carol | A61B 8/12 |
| | | | 600/439 |
| 2015/0112235 A1* | 4/2015 | Brasset | A61N 7/02 |
| | | | 601/3 |
| 2015/0151141 A1* | 6/2015 | Arnal | B06B 3/04 |
| | | | 181/177 |
| 2015/0273246 A1 | 10/2015 | Darlington et al. | |
| 2015/0321027 A1 | 11/2015 | Fedewa et al. | |
| 2016/0235484 A1 | 8/2016 | Carol | |
| 2016/0236013 A1 | 8/2016 | Carol et al. | |
| 2016/0332005 A1 | 11/2016 | Fedewa et al. | |
| 2017/0136266 A1 | 5/2017 | Carol | |
| 2017/0203131 A1 | 7/2017 | Carol et al. | |
| 2017/0303987 A1* | 10/2017 | Horie | A61B 18/00 |

FOREIGN PATENT DOCUMENTS

| | | |
|---|---|---|
| CA | 2662997 C | 1/2016 |
| CN | 106061401 A | 10/2016 |
| EP | 2207596 B1 | 5/2013 |
| EP | 1755458 B1 | 2/2015 |
| EP | 2069018 B1 | 7/2016 |
| EP | 3054858 A1 | 8/2016 |
| EP | 3055027 A1 | 8/2016 |
| EP | 3108934 A1 | 12/2016 |
| HK | 1135345 A1 | 4/2017 |
| JP | 5064386 B2 | 10/2012 |
| JP | 5462167 B2 | 4/2014 |
| JP | 5615548 B2 | 10/2014 |
| JP | 2016533784 A | 11/2014 |
| JP | 6046094 B2 | 12/2016 |
| JP | 2016538014 A | 12/2016 |
| KR | 20160068922 A | 6/2016 |
| WO | 2015054592 A1 | 4/2015 |
| WO | 2015054605 A1 | 4/2015 |
| WO | 2017083133 A1 | 5/2017 |
| WO | 2017127383 A1 | 7/2017 |

OTHER PUBLICATIONS

Hosseini et al., Effects of Gas Pockets on High-Intensity Focused Ultrasound Field, IEEE Transactions on Ultrasonics, Ferroelectrics, and Frequency Control, vol. 58, No. 6, Jun. 2011.
International Search Report and Written Opinion dated Nov. 21, 2017 for International Patent Application No. PCT/US2017/052432 filed Sep. 20, 2017.

* cited by examiner

SYSTEM, APPARATUS AND METHOD FOR HIGH-INTENSITY FOCUSED ULTRASOUND (HIFU) AND/OR ULTRASOUND DELIVERY WHILE PROTECTING CRITICAL STRUCTURES

CROSS-REFERENCE TO RELATED APPLICATION

This application claims priority to U.S. Provisional Application No. 62/398,752, filed Sep. 23, 2016 and titled "Method for High-Intensity Focused Ultrasound (HIFU) Delivery with Protection of Critical Structure," which is herein incorporated by reference.

SUMMARY

HIFU is increasingly being used in a clinical setting for the targeted ablation of tissue in a non-invasive or minimally invasive way in a multitude of therapeutic applications. In order to ablate large tissue volumes in a clinically acceptable period of time, prior art HIFU delivery techniques extend beyond focal ablation and the superposition of elementary or focal HIFU lesions, such as the "always ON" (also known as the "sweeping beam") technique. While clinically effective, such prior art techniques also tend to deliver substantial ultrasonic dose outside of the well-controlled transducer's focal zone, increasing the potential of detrimentally affecting tissues not specifically targeted for ablation.

The presently disclosed technology includes a method to eliminate this undesired ablation post-focally, while still maintaining the benefits of faster HIFU delivery covering large volumes. In one embodiment, the presently disclosed technology can include first creating (controlled) focal lesions covering a portion or sub-volume of the entire volume targeted for ablation, followed by HIFU application using an "always ON" technique to ablate the remaining target volume. The initial focal lesions can change the acoustic tissue properties in such a way as to prevent subsequent HIFU application to propagate beyond this region, effectively protecting post-focal tissue from unintended ablation. Stated differently, one embodiment of the presently disclosed technology includes the creation of elementary lesions that are both part of the treatment and creates a barrier for protection of adjacent tissue (e.g., organs), as well as the subsequent and generally continuous application of HIFU in a trace approach. The elementary lesions both ablate tissue and create a barrier to future or subsequent ablation.

In one embodiment, the presently disclosed technology is directed to a method for delivering HIFU to ablate at least a portion of targeted tissue of a patient and preventing subsequent HIFU application from extending beyond that portion to protect other tissue of the patient. The method can include the steps of moving at least a focal zone of a transducer of a HIFU probe to a first position proximate to targeted tissue of a patient, and supplying power to the transducer to deliver HIFU energy from the transducer to a first portion of the targeted tissue for a first predetermined amount of time to create a first focal lesion and ablate that portion of the targeted tissue. The first focal lesion can act as a barrier for subsequent HIFU ablation of tissue located beyond or behind the first focal lesion thereby protecting tissue beyond or behind the first focal lesion from unintended ablation. The method can include at least temporarily ceasing power to the transducer at the conclusion of the first predetermined amount of time so as to at least temporarily cease delivery of HIFU energy from the transducer to the targeted tissue. The method can include at least slightly moving at least the focal zone of the transducer of the HIFU probe to a second position proximate to the targeted tissue of the patient. The method can include supplying power to the transducer to deliver HIFU energy from the transducer to a second portion of the targeted tissue for a second predetermined amount of time to create a second focal lesion and ablate that portion of the targeted tissue. The second focal lesion can act as a barrier for subsequent HIFU ablation of tissue located beyond or behind the second focal lesion thereby protecting tissue beyond or behind the second focal lesion from unintended ablation. The method can include at least temporarily ceasing power to the transducer at the conclusion of the second predetermined amount of time so as to at least temporarily cease delivery of HIFU energy from the transducer to the targeted tissue. The method can include supplying power to the transducer to deliver HIFU energy from the transducer to the targeted tissue continuously and along a predefined treatment path. The transducer is continuously moving at constant speed and continuously applying HIFU to at least a portion of the targeted tissue.

BRIEF DESCRIPTION OF THE DRAWINGS

The foregoing summary, as well as the following detailed description of the presently disclosed technology, will be better understood when read in conjunction with the appended drawings. For the purpose of illustrating the presently disclosed technology, there are shown in the drawings various illustrative embodiments. It should be understood, however, that the presently disclosed technology is not limited to the precise arrangements and instrumentalities shown. In the drawings.

DETAILED DESCRIPTION

Figure 1A:
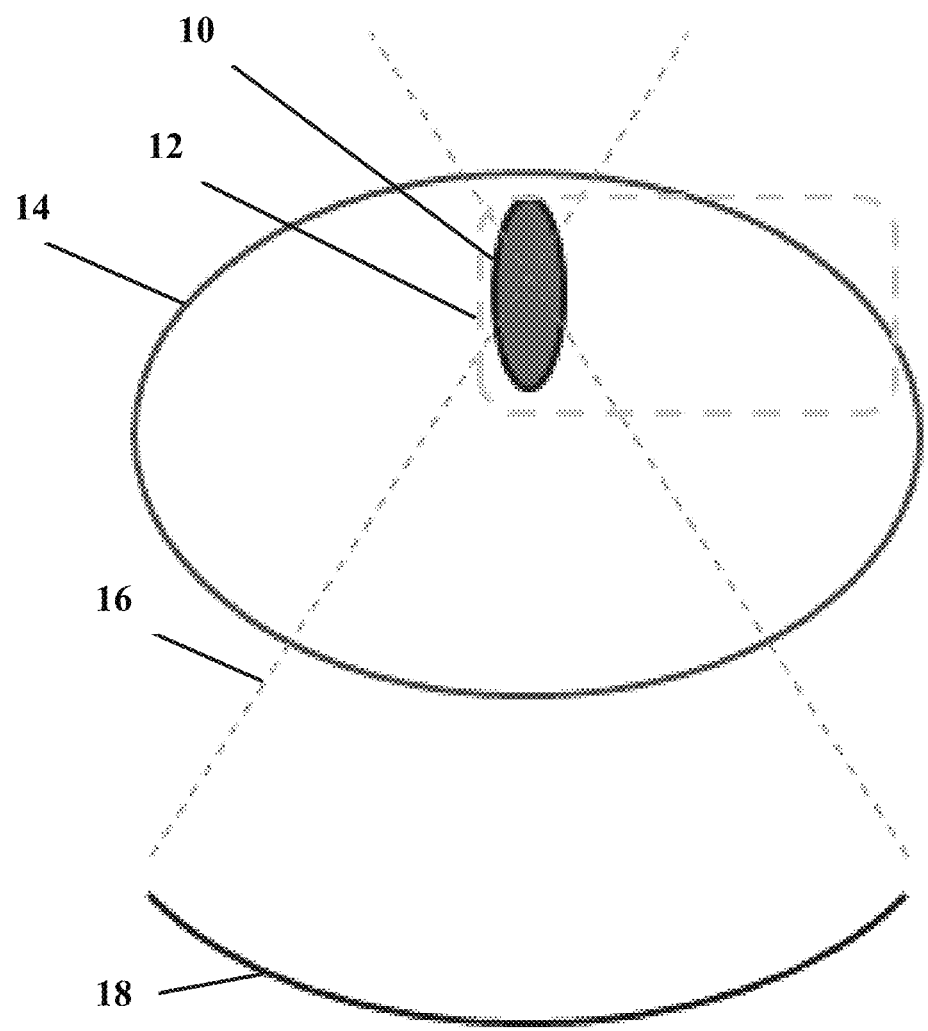
FIG. 1A shows the creation of a single or first focal lesion at time $t=T_{on}$, in accordance with one embodiment of the presently disclosed technology.

While systems, apparatus and methods are described herein by way of examples and embodiments, those skilled in the art recognize that the systems, apparatus and methods of the presently disclosed technology are not limited to the embodiments or drawings described. It should be understood that the drawings and description are not intended to be limited to the particular form disclosed. Rather, the presently disclosed technology covers all modifications, equivalents and alternatives falling within the spirit and scope of the appended claims. Any headings used herein are for organizational purposes only and are not meant to limit the scope of the description or the claims. As used herein, the words "is" and "may" are used in a permissive sense (i.e., meaning having the potential to) rather than the mandatory sense (i.e., meaning must). Similarly, the words "include," "including," and "includes" mean including, but not limited to. Unless specifically set forth herein, the terms "a," "an" and "the" are not limited to one element but instead should be read as meaning "at least one." The terminology includes the words noted above, derivatives thereof and words of similar import.

HIFU can be used in a clinical setting for the targeted ablation of tissue in a non-invasive or minimally invasive way in a multitude of therapeutic applications. Targeted tissue 14 can be ablated by HIFU in a multitude of ways using a probe with a transducer 18, for example.

The generation of a focal lesion, generally designated 10, (i.e., a single lesion, as compared to multiple or compound lesions) can offer the best control for ablating tissue consistently, as its size and location is defined mainly by the HIFU focal zone geometry and HIFU dose (e.g., ultrasound intensity, HIFU ON time–$T_{on}$), parameters that can be easily controlled. Creating focal lesions 10 can be done in a controlled way because their size is predictable, and are primarily defined by the transducer's focal zone size (unlike those generated with other techniques).

Larger volumes can be ablated by using a multitude of focal lesions, each created at a different location in the target tissue 14, and delivered following a pre-determined sequence or treatment plan 12. It is understood by those skilled in the art that the treatment plan 12 can have a predetermined and/or delineated area or volume. The multitude of focal lesions can contact each other in a sequential manner (i.e., such as no space or gap between adjacent focal lesions), or one or more lesions can be separated or spaced-apart. In the latter case, the resulting "wall" or coverage area may not be as good, and any intervening tissue (i.e., that between two spaced-apart focal lesions 10) would not be treated. However, the spaced-apart embodiment may be beneficial in certain applications (e.g., dermatology) where it can be beneficial to leave space so that the tissue can recover.

Figure 1B:
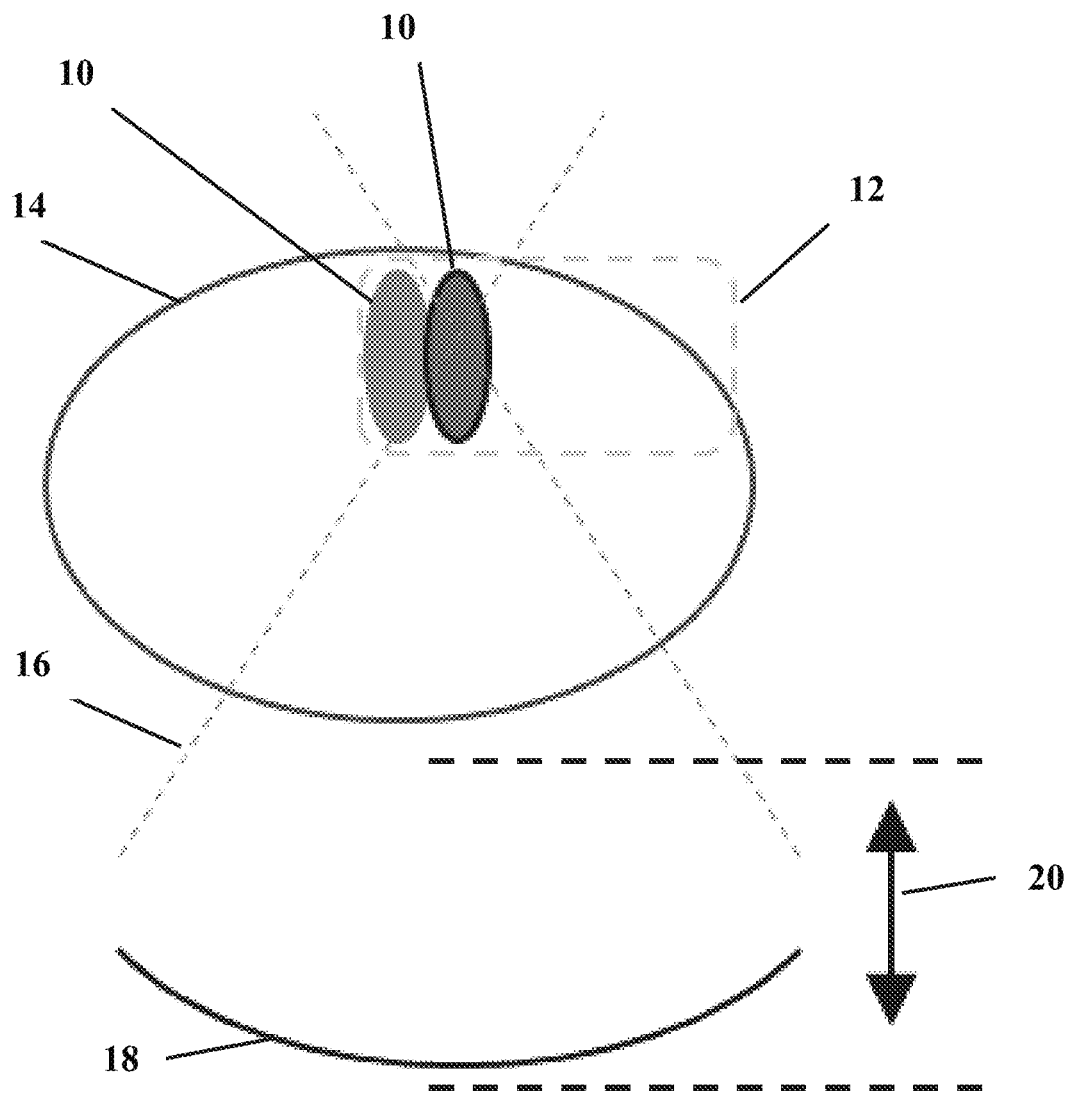
FIG. 1B shows the creation of a second focal lesion next to the first focal lesion at time $t=T_{on}+T_{off}+T_{on}$ in accordance with one embodiment of the presently disclosed technology.
Figure 1C:
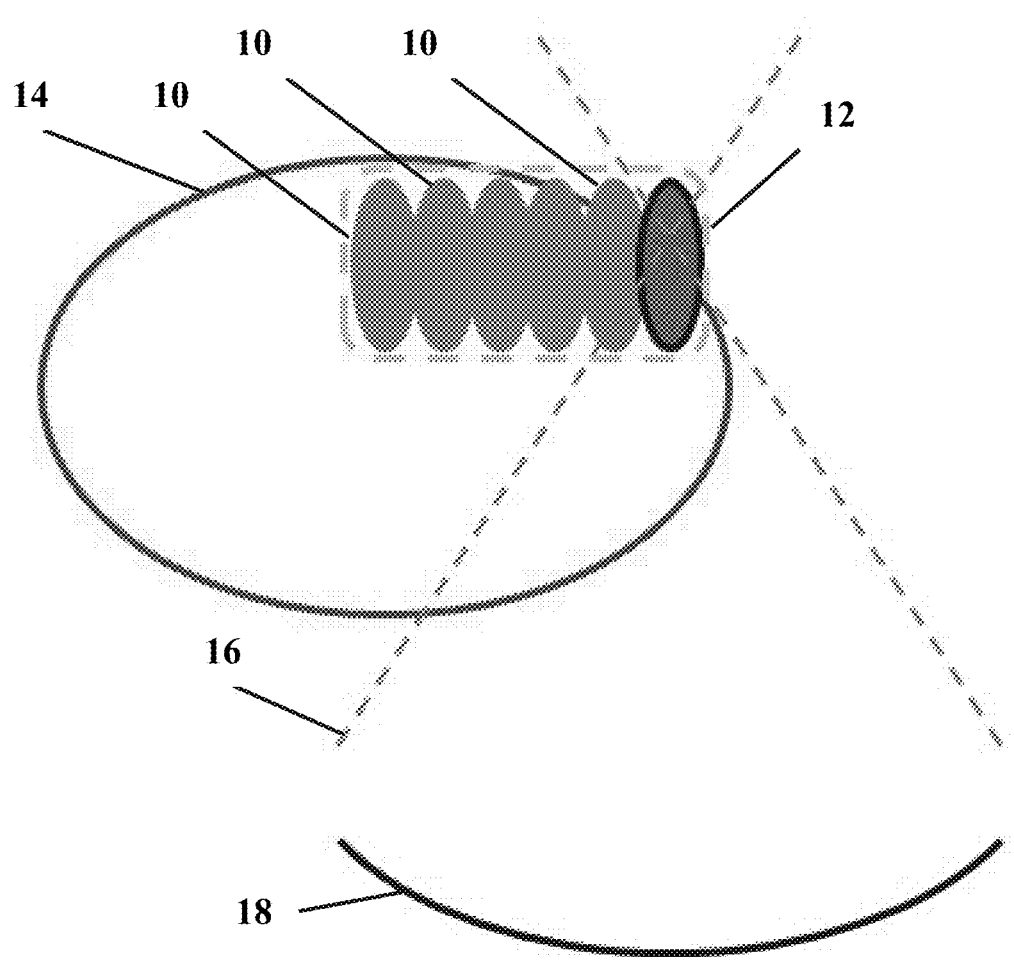
FIG. 1C shows the creation of a multitude of focal lesions after successive HIFU $T_{on}+T_{off}$ cycles in accordance with one embodiment of the presently disclosed technology.

To sustain the ability of the focal lesions 10 to be created consistently (i.e., of similar size and at the desired location), a pause (e.g., HIFU OFF time–$T_{off}$) between successive focal lesions 10 can be employed where HIFU is not being delivered, allowing for tissue cooling. Otherwise, the build-up of thermal dose over time from previously delivered focal lesions 10 while executing the treatment plan 12 can interfere with the creation of future focal lesions 10, as tissue changes during the HIFU application acoustically, mechanically and biologically, compromising the treatment. Changes are largest in the focal zone, but extend beyond it as well, typically encompassing the pre- and post-focal zone regions, or even regions adjacent to or near the focal zone. The terms "pre-focal" and "post-focal" are well known in the art. For example, the term "pre-focal" can be defined as everything in front of (before) the transducer's focal zone. The term "post-focal" can be defined as everything behind (after) the transducer's focal zone. This approach is shown in FIGS. 1A, 1B and 1C.

Figure 1D:
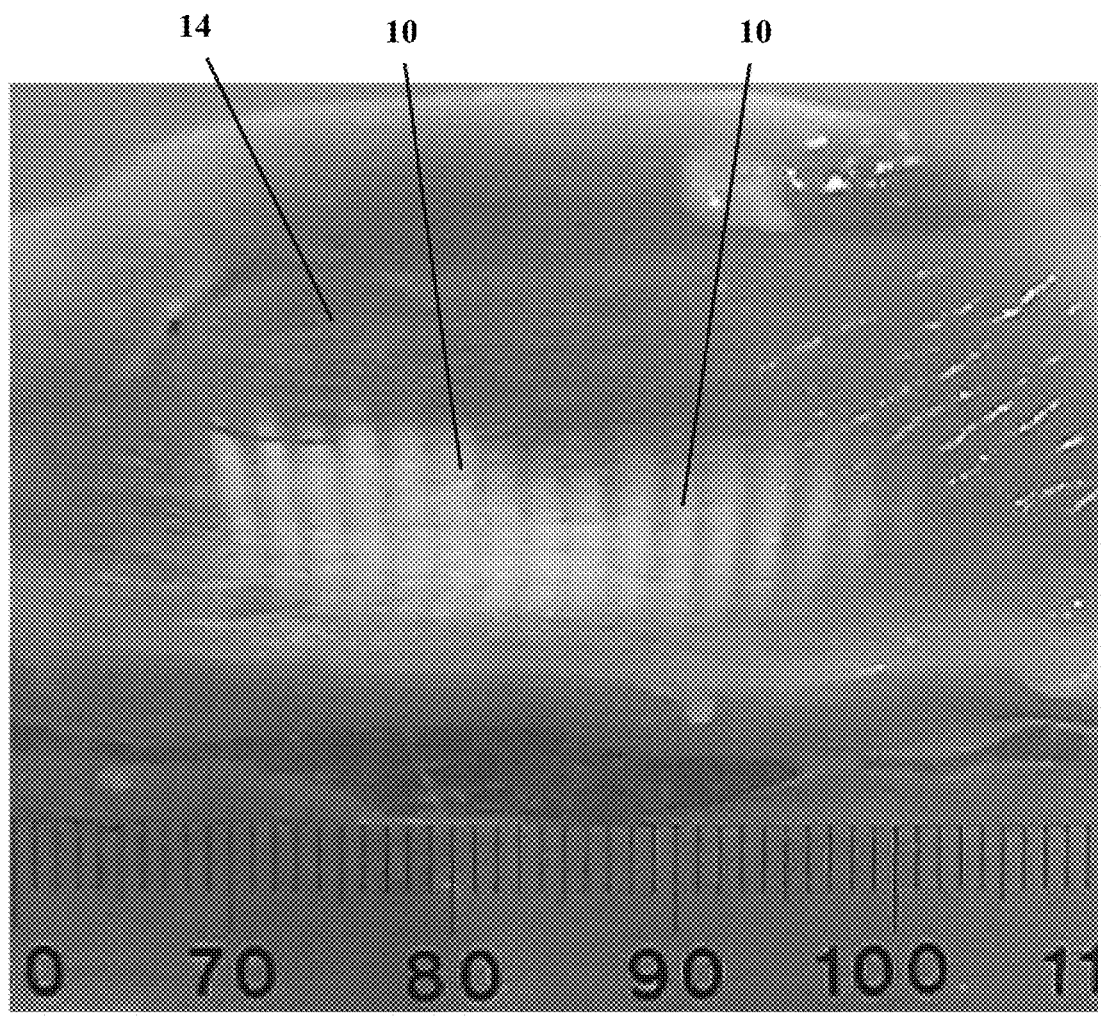
FIG. 1D shows an example of in-vitro tissue ablation via the superposition of focal lesions.

Tissue ablation via the superposition of focal lesions (which are the light or white vertical bands) is shown in FIG. 1D. The advantage of this approach is the ability to ablate tissue in a consistent and controlled manner. HIFU can be delivered this way by the SONABLATE® system, as described in U.S. Patent Application Publication No. 2012/0150035 A1. The disadvantage of this approach is that a large number of focal lesions are typically required to ablate a clinically significant volume, as the transducer's focal zone is usually quite small, resulting in long treatment times.

Figure 2A:
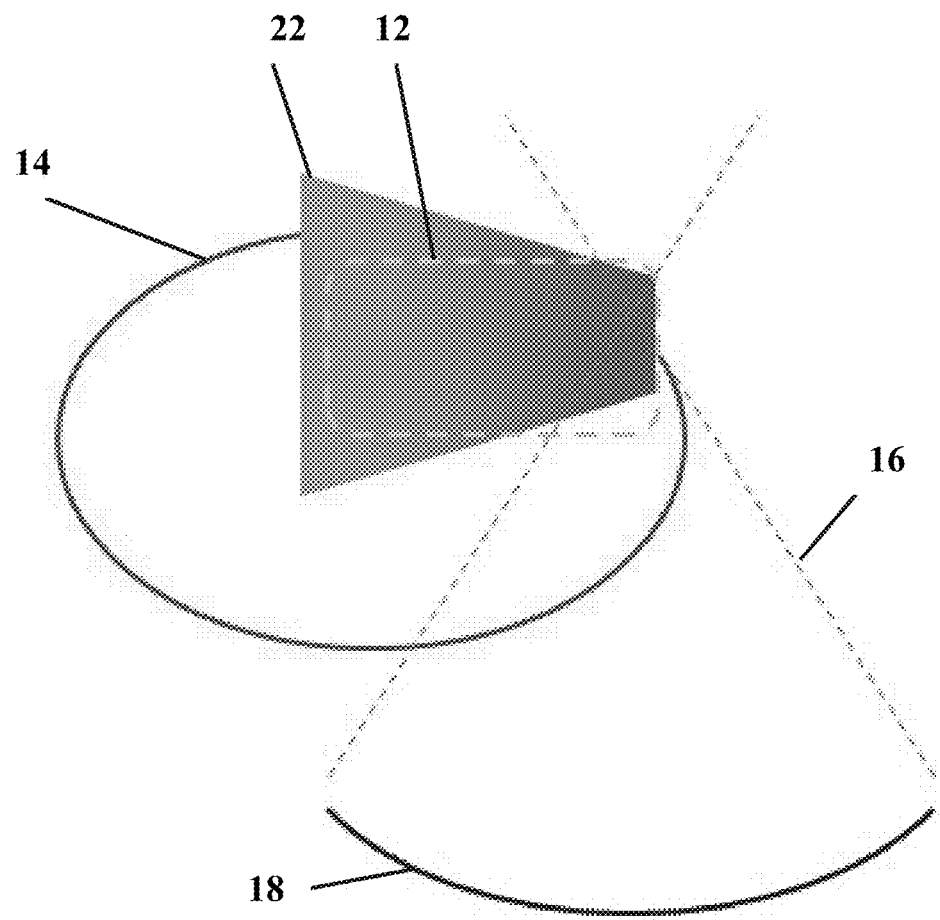
FIG. 2A shows one technique for tissue ablation via a HIFU "always ON" technique.
Figure 2B:
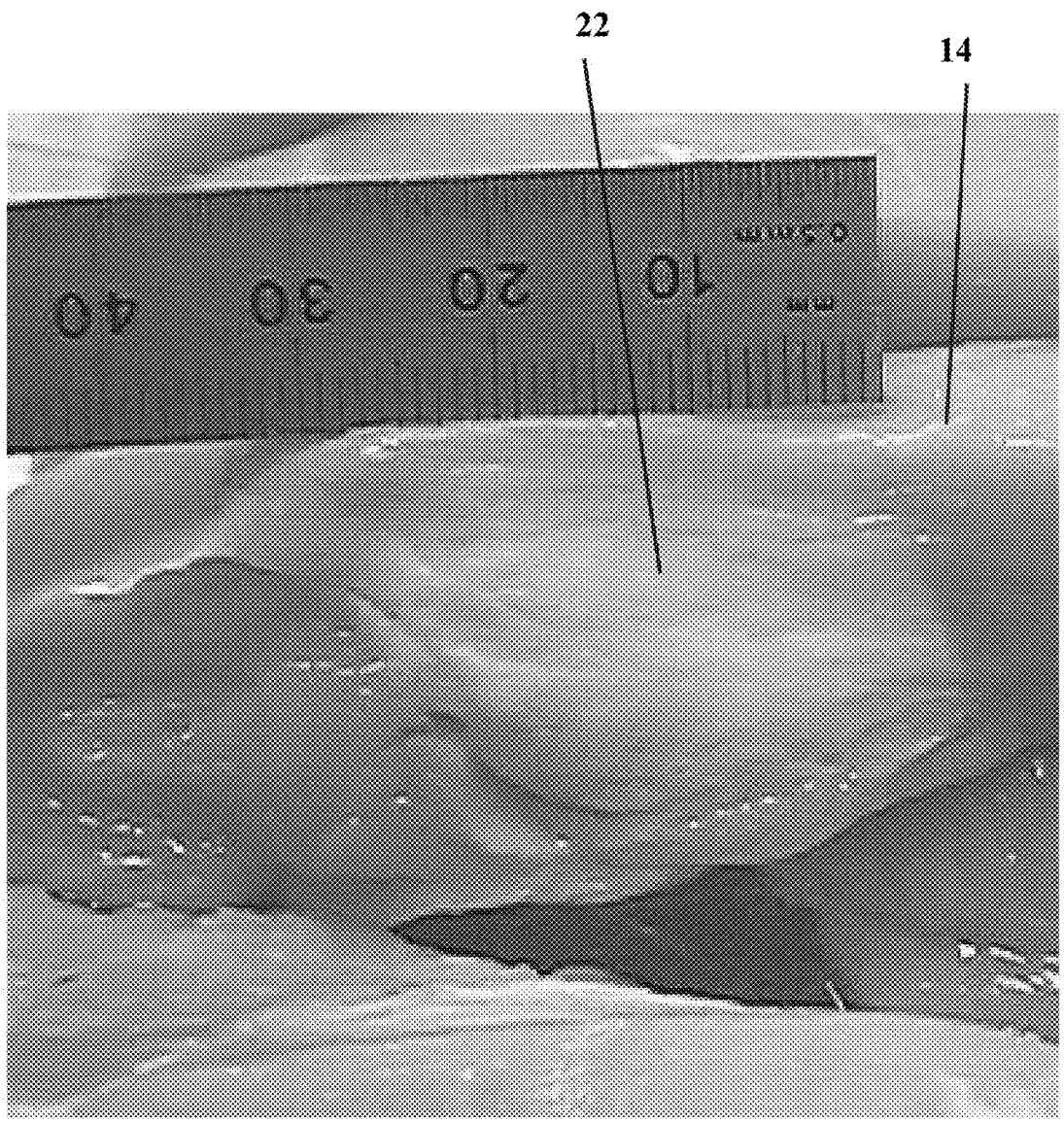
FIG. 2B shows an example of in-vitro tissue ablation using the technique shown in FIG. 2A.

In order to ablate large tissue volumes in a clinically acceptable period of time, HIFU delivery techniques extend beyond focal ablation and the superposition of focal HIFU lesions, such as the technique sometimes referred to as "HIFU always ON." Such a technique is described in U.S. Pat. No. 8,038,631. As disclosed in U.S. Pat. No. 8,038,631, the focused ultrasound transducer (and thus the transducer's focal zone) is continuously and mechanically translated along a pre-defined treatment plan/path while delivering HIFU energy, enabling the ablation of relatively large tissue volumes (see, e.g., reference number 175 of U.S. Pat. No. 8,038,631). This approach is shown in FIG. 2A, and an in-vitro example is shown in FIG. 2B.

When employing the "always ON" technique, treatment times can be reduced, as the volume of tissue ablated over a certain period of time (in $cm^3/s$) is larger (see volume identified by reference number 22) compared to the focal lesion approach. While clinically effective, the "always ON" technique also tends to deliver substantial ultrasonic doses outside of the well-controlled transducer's focal zone and pre-determined treatment plan 12 due to thermal conduction, the absence of a HIFU $T_{off}$ time (preventing tissue temperature recovery during ablation), and increased tissue absorption over time, as focal zone translation speeds tend to be slow (on the order of 1-2 mm/s) in order to achieve reliable ablation, increasing the potential of detrimentally affecting tissues not specifically targeted for ablation. This technique also lends itself well for HIFU applications that benefit from an ablation that extends from the transducer's focal zone plane all the way back to the transducer's surface, i.e., applications in which sparing pre-focal zone tissue is not required. Tissue located post-focally can also, over time, receive an ultrasound dose capable of generating coagulative tissue necrosis with this technique, further reducing the ability to control the delivery of the HIFU energy to a pre-defined target volume.

Solutions that address these issues include the use of non-invasively estimating the tissue temperature using MRI thermometry and calculating the resulting thermal dose, information which is then used to modulate the HIFU energy, treatment plan, or other delivery parameters to minimize ablating tissue located outside of a pre-defined treatment plan. This solution requires the use of an MRI system during the procedure adding to the treatment complexity and cost.

Another technique that can be used includes an acoustically reflective (or absorptive) material between the target volume and the tissue structures that need to be excluded from being insonified by the HIFU, effectively blocking the HIFU energy from reaching these structures and preventing their ablation. This technique can be implemented laparoscopically, for example, by placing a gauze pad (e.g., containing air, which presents an ideal barrier to the ultrasound beam 16) behind a kidney target, to protect critical, important and/or particularly sensitive tissue structures (e.g., one or more organs) located behind the kidney but not part of the treatment plan 12. In other words, a gauze barrier can be placed behind a kidney tumor target to protect the post-focal region from ablation. However, this solution requires the invasive placement of such an acoustic barrier, which is not always possible, and further adds complexity, time, and cost to the procedure.

The presently disclosed technology includes an alternate method to eliminate undesired post-focal ablation, while still maintaining the benefits of faster HIFU delivery covering large volumes. In one embodiment, the presently disclosed technology includes first creating at least one or a plurality of focal lesions covering a portion or sub-volume of the entire volume targeted for ablation, followed by HIFU application using an "always ON" technique to ablate the remaining target volume. In one embodiment, the first step is completed prior to beginning the second step.

The initial focal lesions can be placed with a high degree of accuracy in both their size and location in the initial sub-volume (the sub-volume is generally located around the focal zone of the transducer in depth), as described previously via repeated HIFU $T_{on}$ and $T_{off}$ cycles. The tissue targeted this way undergoes changes in its attenuation (which increases), its absorption (which increases) and its acoustic impedance (change vs. surroundings—can be higher or lower) properties, all part of the tissue ablative process. Because of the tissue property changes due to the ablation, not only is this tissue now ablated, but it can now act as a barrier for subsequent HIFU ablation of tissue located behind it, preventing subsequent HIFU application to propagate beyond this region, effectively protecting post-focal tissue (e.g., critical, important and/or sensitive structure(s) 24) from unintended ablation.

The above-described step(s) is/are distinct from creating bubbles in the focal zone. The presently disclosed technology does not create bubbles. Instead the presently disclosed technology ablates at least a portion of targeted tissue using elementary lesions, which in turn provide a shield for subsequent protection. Bubbles can be undesirable, as they do not allow the tissue to be ablated, can be difficult to control, and sometimes shift the location of the focal lesion to not be located at the focus.

Figure 3A:
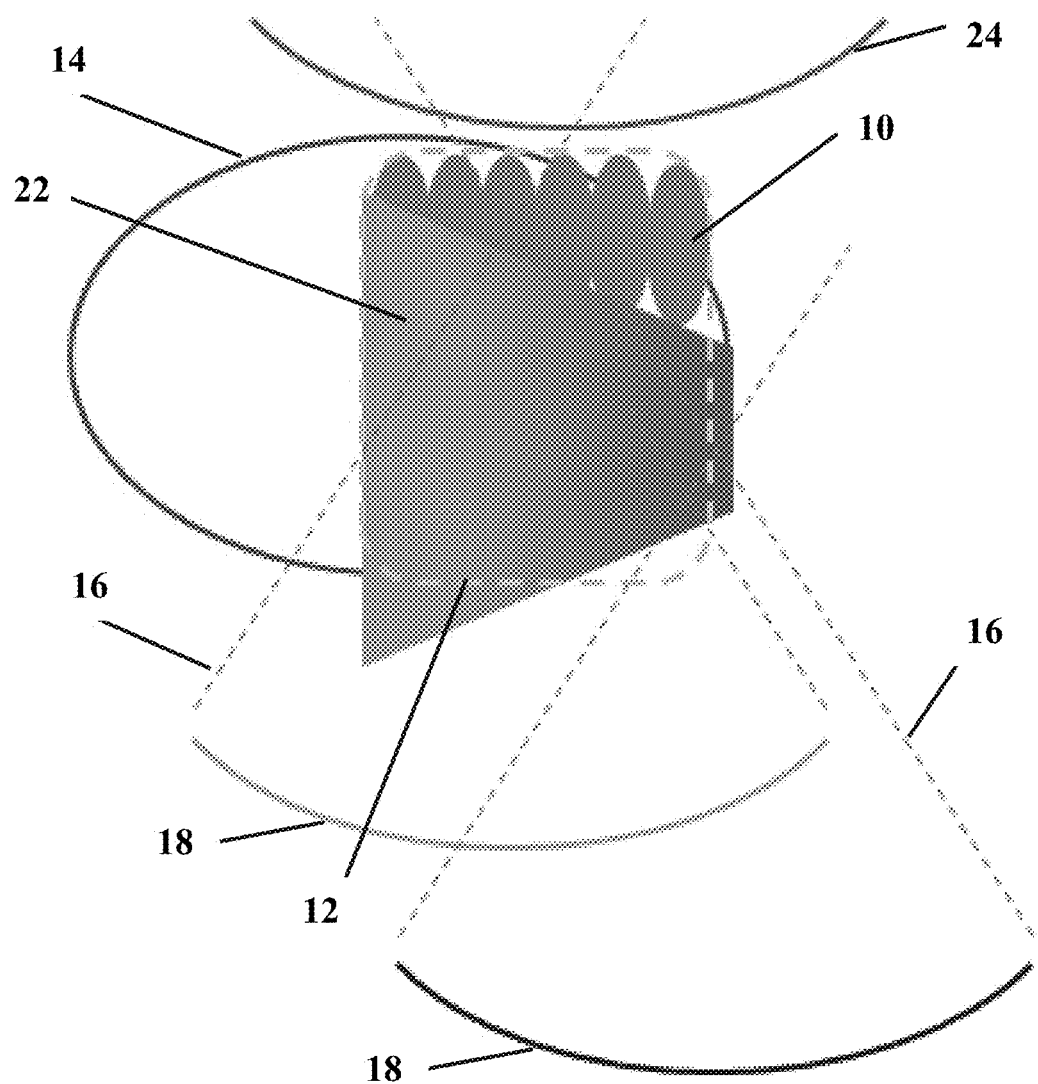
FIG. 3A shows an example of ablation with protection of critical structures in accordance with one embodiment of the presently disclosed technology.

The remaining sub-volume (pre-focal) of the entire volume targeted for ablation 12 is subsequently treated using the "always ON" technique to take advantage of the treatment time gains it offers, without increasing unintended ablation of other regions, protecting critical structures 24 surrounding the target volume. This approach is shown in FIG. 3A.

In one embodiment, the method of the presently disclosed technology can be implemented in any existing HIFU or therapeutic ultrasound system. The presently disclosed technology can be implemented on or with systems having one or more single-element transducers (which can mechanically scan the focal zone to deliver HIFU to a large volume), or with ultrasound arrays (which can electronically scan the transducer's focal zone to deliver HIFU to a large volume), or a combination of both.

As disclosed herein, the concept of using ablated regions to block later or future ultrasound exposure is not taught by the prior art. In one embodiment, the first step of creating one or more focal lesions effectively creates a barrier in one or more specific locations. This barrier of ablated tissue can become hard and generally impenetrable to ultrasound. This barrier allows for the second step of ablating the targeted volume by applying HIFU using an "always ON" technique to be done more quickly, efficiently and/or easier because this second delivery will not propagate behind the initially created barrier at the focal zone.

In one embodiment, steps of the presently disclosed technology can include (in this or another order):

1. Defining a treatment plan 12, which defines the tissue volume targeted for ablation. Because of the barrier that ablated tissue creates to the ultrasound beam propagation, the distal edge of the treatment plan can be specified to coincide with the farthest/deepest (from the transducer's face) focal zone placement location, as otherwise, tissue that is located further distant/deeper won't be able to be effectively treated.

2. Defining a sub-volume in this treatment plan that will be populated with focal lesions. This sub-volume can coincide with the desired location of the acoustic barrier, and can be located between the critical structure(s) 24 that is to be protected and the transducer's face, at the distal edge of the treatment plan 12.

3. The remaining volume of the treatment plan can be ablated using the "always ON" method, and will be located between the focal sub-volume treatment plan and the face of the transducer.

4. Starting the HIFU treatment by delivering the focal lesions first to the previously defined sub-volume, ablating the tissue as desired, and creating the subsequent acoustic barrier. Use sonication parameters that create controllable and repeatable focal lesions (e.g., Focal zone size, Frequency, Lesion spacing, Power, $T_{on}$, $T_{off}$, etc.)

5. When complete, continue with the HIFU treatment by delivering HIFU using the "always ON" mode to the remaining treatment volume of the treatment plan. Sonication parameters can be used that create ablation in this region (e.g., Focal zone size, Frequency, speed of focus translation, trace separation, Power, etc.). The previously created barrier will prevent HIFU energy reaching the post-focal structure, protecting it from ablation.

Figure 3B:
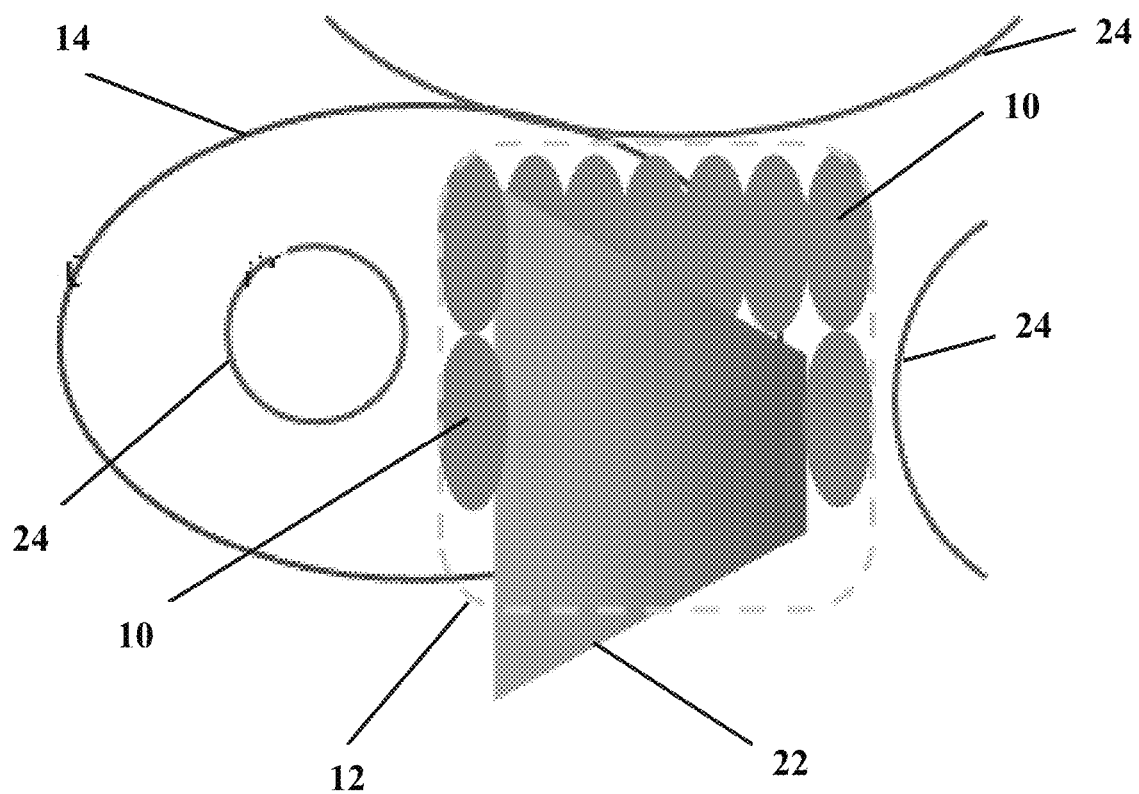
FIG. 3B shows an example of placement of focal lesions for lateral critical structure protection in accordance with one embodiment of the presently disclosed technology.

Alternate embodiments of the present disclosure can include placing a focal lesion sub-volume on the lateral (rather than just at the distal) edge of the planned treatment volume, to offer protection to structures located on the lateral edges of, adjacent to, or near the treatment plan, as shown in FIG. 3B.

Multiple transducers may be used in implementing the presently disclosed technology. A transducer can be used with a geometry optimized to the delivery of focal lesions, and then can be replaced by a second transducer optimized to deliver HIFU using the "always ON" mode. This applies to implementations using arrays and their shaping of the focal zone(s) electronically as well.

The presently disclosed technology does not exclude the (additional) incorporation of either ultrasound or MRI-guidance techniques known in the art for ultrasound treatment guidance, planning, and monitoring, and is compatible with, or can be used in conjunction with, such treatment monitoring and control techniques to increase the reliability and safety of the HIFU delivery.

In all cases, the HIFU delivery sequence can be particularly important. In one embodiment, HIFU delivery should begin distally (with respect to the transducer), and progress towards the face of the transducer. The presently disclosed technology allows for protecting critical structures 24 located distally and laterally with respect to the treatment plan. In one embodiment, the presently disclosed technology is unable to protect critical structures 24 located in the pre-focal zone, as the procedure time gains are achieved with the "always ON" mode of HIFU delivery, which is not suited to allow such protection.

The phrase "always ON" is used in this disclosure to identify a HIFU delivery method that is separate from and/or different to the focal lesion creation method, which achieves 1) tissue necrosis due to both focal ablation and 2) thermal conduction in regions outside of the focal zone. As such, it need not be implemented specifically as "always ON", but could be interspersed with HIFU "OFF" times used for transducer repositioning, treatment monitoring, etc. In such a latter embodiment, the "ON" times can be significantly longer than the "OFF" times. In this disclosure, other variants of this method are not excluded, such as use of a duty cycle to implement the timing, which is at least one example of what would be considered by those of ordinary skill in the art as being "at least substantially continuously" delivering HIFU. In one embodiment of the presently disclosed technology, the differentiating factor is its delivery of energy that results in a lesion or ablated volume significantly larger than those that can be controllably created via elementary/focal lesion techniques.

Figure 3C:
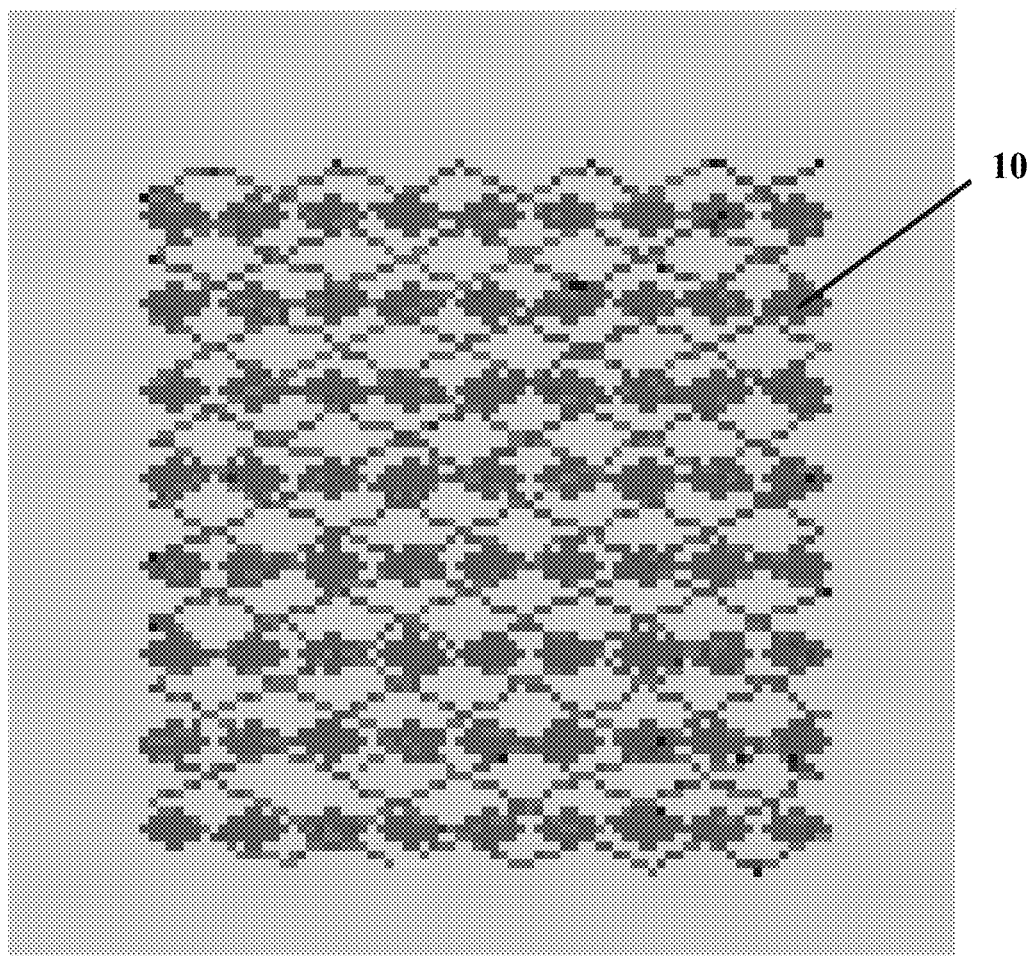
FIG. 3C shows one example of focal lesion locations and "always ON" trace pattern according to one embodiment of the presently disclosed technology.

An example of a specific embodiment that can utilize the presently disclosed technology includes laparoscopic HIFU kidney ablation using the SONATHERM® system. This device uses an f/1 35 mm×11 mm aperture truncated spherical shell transducer operating at 4 MHz. "F/1" stands for an f-number of 1, meaning that the focal length of the transducer is the same as the aperture. Protective focal lesions can be created at the distal region of the treatment plan at a power level of exactly or approximately 34 W (with a 15 mm water standoff 20 (see, e.g., FIG. 1B) between the transducer and the kidney), with $T_{on}=2$ s and $T_{off}=2$ seconds, each separated by 3 mm from each other. The "always ON" lesion can be created following the placement of focal lesions, with a power level of exactly or approximately 34 W. The trace speed can be 1.3 mm/s, and the trace separation can be 1.3 mm. These settings allow for the creation of a complete ablation volume extending from a tissue depth of 25 mm all the way to the tissue surface. When the water standoff between the transducer and kidney is increased to exactly or approximately 20 mm, the acoustic power can be reduced to approximately 29-30 W with similar settings. FIG. 3C shows a representative cross-sectional pattern of focal lesion locations (dots or oval shaped markings), and the trace followed by the transducer's focal zone during the "always ON" mode of operation.

Additional examples of the presently disclosed technology include the creation of focal lesions utilizing a truncated spherical shell transducer operating at or approximately 4 MHz, with an aperture of exactly or approximately 30×22 mm, and a radius of curvature of exactly or approximately 40 mm, operating at a total acoustic power level of exactly or approximately 37 W (with a 10 mm water standoff), with $T_{on}=3$ seconds and $T_{off}=6$ seconds, creating focal lesions separated by exactly or approximately 3 mm from each other. The "always ON" sonication parameters include a power level of exactly or approximately 37 W, a trace speed of exactly or approximately 1.0 mm/s, and a trace separation of exactly or approximately 1.1 mm.

In-vivo experiments performed indicate that the power level for creating the focal lesions tends to be similar to that required to generate a reliable ablation volume using the "always ON" technique. It is understood, however, that these do not need to be similar, and can be optimized for their respective delivery technique, as required.

When single-element transducers are used as described, the transducer should be mechanically translated in order to position its focal zone at the desired locations. This can be accomplished with transducer motor systems. Alternatively, the transducer may remain stationary, and the target translated, as needed. When array devices are used as described, their focal zone may be translated electronically (via electronic focusing and beam steering techniques known in the art), or via a combination of both electronic and mechanical focal zone translation, should the required focal zone location exceed the electronic focusing capability of the array, for example.

The systems, method and processes described can be implemented in any and all HIFU systems that could benefit from additional features that increase treatment safety (by protecting critical structures 24 from receiving a lethal HIFU dose), simplify the workflow of the procedure, and treatment time reduction. For example, they are being considered for implementation in SonaCare Medical's SONATHERM® product, for the laparoscopic ablation of tissue from the focal zone all the way to the surface of the target tissue.

Figure 4:
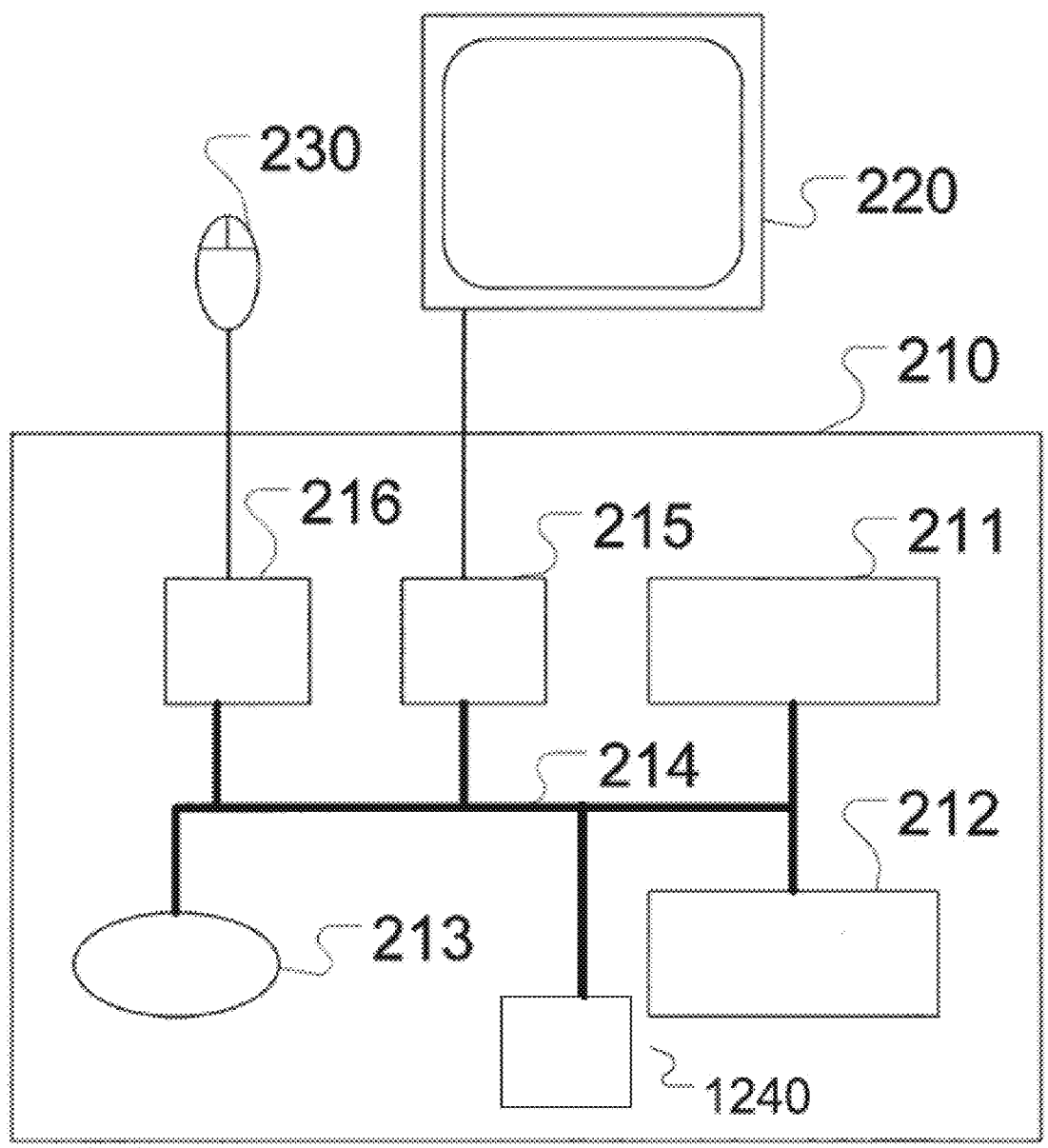
FIG. 4 is schematic diagram of a computing system of one embodiment of the present disclosure.

One or more of the above-described techniques and/or embodiments can be implemented with or involve software, for example modules executed on one or more computing devices 210 (see FIG. 4). Of course, modules described herein illustrate various functionalities and do not limit the structure or functionality of any embodiments. Rather, the functionality of various modules may be divided differently and performed by more or fewer modules according to various design considerations.

Each computing device 210 may include one or more processing devices 211 designed to process instructions, for example computer readable instructions (i.e., code), stored in a non-transient manner on one or more storage devices 213. By processing instructions, the processing device(s) 211 may perform one or more of the steps and/or functions disclosed herein. Each processing device may be real or virtual. In a multi-processing system, multiple processing units may execute computer-executable instructions to increase processing power.

The storage device(s) 213 may be any type of non-transitory storage device (e.g., an optical storage device, a magnetic storage device, a solid state storage device, etc.). The storage device(s) 213 may be removable or non-removable, and may include magnetic disks, magneto-optical disks, magnetic tapes or cassettes, CD-ROMs, CD-RWs, DVDs, BDs, SSDs, or any other medium which can be used to store information. Alternatively, instructions may be stored in one or more remote storage devices, for example storage devices accessed over a network or the internet.

Each computing device 210 additionally may have memory 212, one or more input controllers 216, one or more output controllers 215, and/or one or more communication connections 1240. The memory 212 may be volatile memory (e.g., registers, cache, RAM, etc.), non-volatile memory (e.g., ROM, EEPROM, flash memory, etc.), or some combination thereof. In at least one embodiment, the memory 212 may store software implementing described techniques.

An interconnection mechanism 214, such as a bus, controller or network, may operatively couple components of the computing device 210, including the processor(s) 211, the memory 212, the storage device(s) 213, the input controller(s) 216, the output controller(s) 215, the communication connection(s) 1240, and any other devices (e.g., network controllers, sound controllers, etc.). The output controller(s) 215 may be operatively coupled (e.g., via a wired or wireless connection) to one or more output devices 220 (e.g., a monitor, a television, a mobile device screen, a touch-display, a printer, a speaker, etc.) in such a fashion that the output controller(s) 215 can transform the display on the output device 220 (e.g., in response to modules executed). The input controller(s) 216 may be operatively coupled (e.g., via a wired or wireless connection) to one or more input devices 230 (e.g., a mouse, a keyboard, a touch-pad, a scroll-ball, a touch-display, a pen, a game controller, a voice input device, a scanning device, a digital camera, etc.) in such a fashion that input can be received from a user.

The communication connection(s) 1240 may enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

FIG. 4 illustrates the computing device 210, the output device 220, and the input device 230 as separate devices for ease of identification only. However, the computing device 210, the output device(s) 220, and/or the input device(s) 230 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). The computing device 210 may be one or more servers, for example a farm of networked servers, a clustered server environment, or a cloud service running on remote computing devices.

The above disclosed methods and description of a generic embodiment of the presently disclosed technology are provided to enable any person skilled in the art to make or use the invention. Various modifications to the embodiments described herein will be readily apparent to those skilled in the art, and the generic principles described herein can be applied to other embodiments without departing from the spirit or scope of the presently disclosed technology. Thus, it is to be understood that the description and drawings presented herein represent a functional generic embodiment of the presently disclosed technology and are, therefore, representative of the subject matter which is broadly contemplated by the presently disclosed technology. It is further understood that the scope of the presently disclosed technology fully encompasses other embodiments that may become obvious to those skilled in the art and that the scope of the presently disclosed technology is accordingly limited by nothing other than the appended claims.

We claim:

1. A method for delivering High-Intensity Focused Ultrasound (HIFU) to ablate at least a portion of targeted tissue of a patient and preventing subsequent HIFU application from extending beyond that portion to protect other tissue of the patient, the method comprising the steps of:
   a) moving at least a focal zone of a transducer of a HIFU probe to a first position proximate to targeted tissue of a patient;
   b) supplying power to the transducer to deliver HIFU energy from the transducer to a first portion of the targeted tissue for a first predetermined amount of time to create a first focal lesion and ablate that portion of the targeted tissue, wherein the first focal lesion acts as a barrier for subsequent HIFU ablation of tissue located beyond or behind the first focal lesion thereby protecting tissue beyond or behind the first focal lesion from unintended ablation;
   c) at least temporarily ceasing power to the transducer at the conclusion of the first predetermined amount of time so as to at least temporarily cease delivery of HIFU energy from the transducer to the targeted tissue;
   d) at least slightly moving at least the focal zone of the transducer of the HIFU probe to a second position proximate to the targeted tissue of the patient;
   e) supplying power to the transducer to deliver HIFU energy from the transducer to a second portion of the targeted tissue for a second predetermined amount of time to create a second focal lesion and ablate that portion of the targeted tissue, wherein the second focal lesion acts as a barrier for subsequent HIFU ablation of tissue located beyond or behind the second focal lesion thereby protecting tissue beyond or behind the second focal lesion from unintended ablation;
   f) at least temporarily ceasing power to the transducer at the conclusion of the second predetermined amount of time so as to at least temporarily cease delivery of HIFU energy from the transducer to the targeted tissue; and
   g) supplying power to the transducer to deliver HIFU energy from the transducer to the targeted tissue continuously and along a predefined treatment path, wherein the transducer is continuously moving at constant speed and continuously applying HIFU to at least a portion of the targeted tissue.

2. The method of claim 1, wherein the first focal lesion is spaced-apart from the second focal lesion.

3. The method of claim 1, wherein the first focal lesion contacts the second focal lesion.

4. The method of claim 1, wherein the transducer is a single-element transducer configured to mechanically scan a focal zone through at least a portion of the targeted tissue to deliver HIFU.

5. The method of claim 1, wherein the transducer is an array of transducers that electronically scan a focal zone through at least a portion of the targeted tissue to deliver HIFU.

6. The method of claim 1, further comprising:
   prior to step g) providing power to the transducer so as to deliver HIFU energy from the transducer to a third portion of the targeted tissue for a predetermined amount of time to create a third focal lesion and ablate that portion of the targeted tissue, wherein the third focal lesion acts as a barrier for subsequent HIFU ablation of tissue located beyond or behind the third focal lesion thereby protecting tissue beyond or behind the third focal lesion from unintended ablation.

7. The method of claim 6, wherein the second focal lesion is spaced-apart from the third focal lesion.

8. The method of claim 6, wherein the second focal lesion contacts the third focal lesion, and wherein the first focal lesion is spaced-apart from the third focal lesion.

9. A method for delivering ultrasound, the method comprising the steps of:
   a) positioning at least a focal zone of a transducer of an ultrasound probe proximate to targeted tissue of a patient;
   b) supplying power to the transducer to deliver ultrasound energy from the transducer to a first portion of the targeted tissue for a predetermined amount of time to create a first focal lesion in the targeted tissue;
   c) at least temporarily ceasing power to the transducer so as to at least temporarily cease delivery of ultrasound energy from the transducer to the targeted tissue;

d) supplying power to the transducer to deliver ultrasound energy from the transducer to a second portion of the targeted tissue for a predetermined amount of time to create a second focal lesion in the targeted tissue;

e) at least temporarily ceasing power to the transducer so as to at least temporarily cease delivery of ultrasound energy from the transducer to the targeted tissue; and f) supplying power to the transducer to deliver ultrasound energy from the transducer to the targeted tissue at least substantially continuously and along a predefined treatment path.

10. The method of claim 9, wherein in step f) the focal zone of the transducer is continuously moving at constant speed and at least substantially continuously applying ultrasound to at least a portion of the targeted tissue.

11. The method of claim 9, wherein the first focal lesion is spaced-apart from the second focal lesion.

12. The method of claim 9, wherein the first focal lesion contacts the second focal lesion.

13. The method of claim 9, wherein tissue consumed by the focal lesions is ablated, and wherein each focal lesion acts as a barrier for subsequent ultrasound ablation of tissue located beyond or behind the respective focal lesion thereby protecting tissue beyond or behind the respective focal lesion from unintended ablation.

14. The method of claim 9, wherein the transducer is a single-element transducer configured to mechanically scan a focal zone through at least a portion of the targeted tissue to deliver ultrasound.

15. The method of claim 9, wherein the transducer is an array of transducers that electronically scan a focal zone through at least a portion of the targeted tissue to deliver ultrasound.

16. A system for treating a targeted area of tissue with High-Intensity Focused Ultrasound (HIFU), the system comprising:

a probe having a probe tip and a housing formed to include an aperture therein, a transducer coupled to the probe, the transducer being configured to emit ultrasound energy through the aperture in the housing to deliver HIFU energy to a focal zone located within the targeted area, the probe tip being positionable to deliver HIFU energy to the targeted area, a controller configured to supply power to the transducer to deliver HIFU energy from the transducer to a first portion of the targeted tissue for a first predetermined amount of time to create a first focal lesion and ablate that portion of the targeted tissue, the first focal lesion acting as a barrier for subsequent HIFU ablation of tissue located beyond or behind the first focal lesion thereby protecting tissue beyond or behind the first focal lesion from unintended ablation, wherein the controller at least temporarily ceases power to the transducer at the conclusion of the first predetermined amount of time so as to at least temporarily cease delivery of HIFU energy from the transducer to the targeted tissue, wherein the controller supplies power to the transducer to deliver HIFU energy from the transducer to a second portion of the targeted tissue for a second predetermined amount of time to create a second focal lesion and ablate that portion of the targeted tissue, wherein the second focal lesion acts as a barrier for subsequent HIFU ablation of tissue located beyond or behind the second focal lesion thereby protecting tissue beyond or behind the second focal lesion from unintended ablation, wherein the controller at least temporarily ceases power to the transducer at the conclusion of the second predetermined amount of time so as to at least temporarily cease delivery of HIFU energy from the transducer to the targeted tissue, the controller providing power to the transducer to deliver HIFU energy from the transducer to the targeted tissue substantially continuously and along a predefined treatment path, and wherein the focal zone of the transducer is continuously moving at constant speed and at least substantially continuously applying ultrasound to at least a portion of the targeted tissue.

17. The system of claim 16, wherein the transducer is a single-element transducer configured to mechanically scan a focal zone through at least a portion of the targeted tissue to deliver HIFU.

18. The system of claim 16, wherein the transducer is an array of transducers that electronically scan a focal zone through at least a portion of the targeted tissue to deliver HIFU.

19. The system of claim 16, wherein the first focal lesion is spaced-apart from the second focal lesion.

20. The system of claim 16, wherein the first focal lesion contacts the second focal lesion.

* * * * *